(12) United States Patent
Ullrich

(10) Patent No.: US 12,425,415 B2
(45) Date of Patent: *Sep. 23, 2025

(54) DELAYED AND PROVISIONAL USER AUTHENTICATION FOR MEDICAL DEVICES

(71) Applicant: Meinhard Dieter Ullrich, Lexington, MA (US)

(72) Inventor: Meinhard Dieter Ullrich, Lexington, MA (US)

(73) Assignee: Imprivata, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/492,973

(22) Filed: Oct. 24, 2023

(65) Prior Publication Data

US 2024/0089266 A1 Mar. 14, 2024

Related U.S. Application Data

(63) Continuation of application No. 17/714,413, filed on Apr. 6, 2022, now Pat. No. 11,838,295, and a continuation of application No. 16/414,943, filed on May 17, 2019, now Pat. No. 11,329,990.

(51) Int. Cl.
*H04L 9/40* (2022.01)
*G06F 21/31* (2013.01)
*G16H 40/40* (2018.01)

(52) U.S. Cl.
CPC ............ *H04L 63/108* (2013.01); *G06F 21/31* (2013.01); *G16H 40/40* (2018.01); *G06F 2221/2101* (2013.01); *G06F 2221/2151* (2013.01)

(58) Field of Classification Search
CPC . H04L 63/108; H04L 2463/121; H04L 63/08; G06F 21/31; G06F 2221/2101; G06F 2221/2151; G06F 2221/2137; G16H 40/40; G16H 40/63
See application file for complete search history.

(56) References Cited

U.S. PATENT DOCUMENTS

| | | | |
|---|---|---|---|
| 5,857,020 A | 1/1999 | Peterson, Jr. | |
| 6,467,090 B1 * | 10/2002 | Brodigan | H04N 21/25833 725/98 |
| 6,609,198 B1 | 8/2003 | Wood et al. | |
| 7,966,649 B1 * | 6/2011 | Cooper | H04L 9/3228 726/17 |

(Continued)

*Primary Examiner* — Aravind K Moorthy
(74) *Attorney, Agent, or Firm* — Morgan, Lewis & Bockius LLP

(57) ABSTRACT

Representative embodiments of operating a secured device requiring user authentication include receiving a request from a user for operating the device without prior authentication; granting the user temporary access to the device in accordance with a security policy that specifies a predetermined time interval and/or a predetermined number of device operations within which authentication must occur to continue at least some operations of the device; computationally storing an audit trail identifying the temporary access and actions performed during the temporary access; and upon determining that authentication has not been provided within the predetermined time interval or number of device operations, preventing at least some operations of the device and updating the audit trail to specify expiration of the temporary access.

20 Claims, 5 Drawing Sheets

(56) References Cited

U.S. PATENT DOCUMENTS

| | | | |
|---|---|---|---|
| 8,065,712 B1* | 11/2011 | Cheng | H04L 63/105 |
| | | | 726/4 |
| 8,800,008 B2 | 8/2014 | Sturtevant et al. | |
| 8,819,763 B1 | 8/2014 | Cheung et al. | |
| 9,047,458 B2 | 6/2015 | Etchegoyen | |
| 9,332,434 B1 | 5/2016 | Dotan et al. | |
| 9,438,580 B2* | 9/2016 | Kupper | H04L 9/3271 |
| 9,471,533 B1* | 10/2016 | Roth | H04L 67/5682 |
| 9,603,019 B1* | 3/2017 | Ramatchandirane | |
| | | | G06Q 20/383 |
| 9,641,880 B1 | 5/2017 | Scurtu et al. | |
| 9,935,931 B2* | 4/2018 | Chudy | H04L 63/08 |
| 10,182,044 B1* | 1/2019 | Praus | H04L 63/0428 |
| 10,250,612 B1* | 4/2019 | Raposa | H04L 63/108 |
| 10,439,825 B1* | 10/2019 | Meyer | H04L 9/321 |
| 10,673,862 B1* | 6/2020 | Threlkeld | G06F 21/62 |
| 10,715,514 B1* | 7/2020 | Threlkeld | H04L 63/0807 |
| 10,791,119 B1 | 9/2020 | Coleman | |
| 11,329,990 B2* | 5/2022 | Ullrich | H04L 63/108 |
| 11,838,295 B2* | 12/2023 | Ullrich | G16H 40/40 |
| 2002/0062451 A1* | 5/2002 | Scheidt | H04L 9/0825 |
| | | | 726/7 |
| 2002/0091946 A1* | 7/2002 | Satoh | G06F 1/3203 |
| | | | 726/5 |
| 2003/0041268 A1 | 2/2003 | Hashimoto | |
| 2004/0015367 A1 | 1/2004 | Nicastro | |
| 2004/0107360 A1 | 6/2004 | Herrman et al. | |
| 2004/0120330 A1* | 6/2004 | Rhine | H04L 12/44 |
| | | | 370/408 |
| 2004/0225891 A1* | 11/2004 | Kang | H04L 63/0428 |
| | | | 713/193 |
| 2004/0240444 A1* | 12/2004 | Matthews | H04L 51/234 |
| | | | 370/389 |
| 2005/0038869 A1* | 2/2005 | Zimler | G06F 15/16 |
| | | | 709/217 |
| 2006/0168647 A1* | 7/2006 | Chiloyan | H04W 12/082 |
| | | | 726/4 |
| 2006/0248597 A1* | 11/2006 | Keneman | G06F 1/1647 |
| | | | 726/27 |
| 2007/0043786 A1 | 2/2007 | DiFalco et al. | |
| 2007/0101345 A1* | 5/2007 | Takagi | G06F 9/4411 |
| | | | 719/321 |
| 2007/0136581 A1 | 6/2007 | Hoghaug et al. | |
| 2007/0253553 A1 | 11/2007 | Abdul Rahman | |
| 2008/0052778 A1 | 2/2008 | Narusawa et al. | |
| 2008/0180276 A1* | 7/2008 | Sigtermans | G01D 18/00 |
| | | | 340/870.16 |
| 2009/0204956 A1* | 8/2009 | Branda | G06F 21/10 |
| | | | 717/168 |
| 2009/0254995 A1* | 10/2009 | John | G06F 21/74 |
| | | | 726/27 |
| 2010/0071027 A1* | 3/2010 | Agulnik | H04W 4/08 |
| | | | 726/1 |
| 2010/0115587 A1 | 5/2010 | Kubota et al. | |
| 2010/0161928 A1 | 6/2010 | Sela et al. | |
| 2010/0169965 A1* | 7/2010 | Chhabra | G06F 21/88 |
| | | | 726/17 |
| 2010/0325710 A1* | 12/2010 | Etchegoyen | G06F 21/31 |
| | | | 726/7 |
| 2011/0302117 A1 | 12/2011 | Pinckney et al. | |
| 2012/0089732 A1 | 4/2012 | Clark | |
| 2012/0117209 A1 | 5/2012 | Sinha | |
| 2012/0123219 A1* | 5/2012 | Georgiev | A61B 5/08 |
| | | | 715/764 |
| 2013/0081114 A1 | 3/2013 | Bell et al. | |
| 2013/0133051 A1 | 5/2013 | Riemers | |
| 2013/0167207 A1* | 6/2013 | Davis | G06F 21/316 |
| | | | 726/5 |
| 2013/0254401 A1 | 9/2013 | Marshall et al. | |
| 2013/0291093 A1 | 10/2013 | Matsuoka | |
| 2013/0318573 A1 | 11/2013 | Reunamaki et al. | |
| 2013/0318604 A1 | 11/2013 | Coates et al. | |
| 2014/0020071 A1* | 1/2014 | Jannelli | G06F 21/335 |
| | | | 726/5 |
| 2014/0143295 A1 | 5/2014 | Girsch et al. | |
| 2014/0181998 A1 | 6/2014 | Hunt et al. | |
| 2014/0222450 A1* | 8/2014 | Gray | A61M 5/142 |
| | | | 705/2 |
| 2014/0330944 A1 | 11/2014 | Dabbiere et al. | |
| 2014/0350349 A1 | 11/2014 | Geurts et al. | |
| 2014/0366080 A1 | 12/2014 | Gupta et al. | |
| 2015/0089590 A1* | 3/2015 | Krishnan | A61N 1/37254 |
| | | | 607/59 |
| 2015/0099480 A1* | 4/2015 | Reiter | H04W 4/027 |
| | | | 455/418 |
| 2015/0227727 A1* | 8/2015 | Grigg | H04W 12/63 |
| | | | 726/4 |
| 2015/0242576 A1* | 8/2015 | Tounooka | G16H 10/60 |
| | | | 705/2 |
| 2015/0288668 A1* | 10/2015 | Kupper | H04L 67/306 |
| | | | 726/4 |
| 2016/0045661 A1* | 2/2016 | Gray | A61M 5/142 |
| | | | 604/67 |
| 2016/0073253 A1* | 3/2016 | Grodin | H04W 48/04 |
| | | | 455/418 |
| 2016/0253689 A1 | 9/2016 | Milton | |
| 2016/0277411 A1* | 9/2016 | Dani | G06F 21/6218 |
| 2016/0345170 A1 | 11/2016 | Mann | |
| 2016/0352752 A1 | 12/2016 | Bush et al. | |
| 2016/0357981 A1* | 12/2016 | Tzeng | G06F 21/629 |
| 2017/0018130 A1* | 1/2017 | Robinson | G07C 9/28 |
| 2017/0041303 A1* | 2/2017 | Trimmer | H04L 63/061 |
| 2017/0052522 A1 | 2/2017 | Klein et al. | |
| 2017/0173262 A1 | 6/2017 | Veltz | |
| 2017/0244864 A1* | 8/2017 | Ishino | H04N 1/4433 |
| 2017/0257360 A1 | 9/2017 | Gattu | |
| 2017/0279733 A1 | 9/2017 | Marshall et al. | |
| 2017/0289173 A1 | 10/2017 | Resch et al. | |
| 2017/0346710 A1* | 11/2017 | Jones-McFadden | G06Q 40/02 |
| 2018/0007059 A1 | 1/2018 | Innes et al. | |
| 2018/0041930 A1 | 2/2018 | Hampel et al. | |
| 2018/0054428 A1 | 2/2018 | Appel et al. | |
| 2018/0061158 A1* | 3/2018 | Greene | G06V 20/52 |
| 2018/0075247 A1 | 3/2018 | Campero et al. | |
| 2018/0114015 A1* | 4/2018 | Nuseibeh | H04L 67/1095 |
| 2018/0115130 A1* | 4/2018 | Truluck | G06F 21/30 |
| 2018/0139205 A1 | 5/2018 | Devaney et al. | |
| 2018/0183806 A1 | 6/2018 | Nambisan | |
| 2018/0211005 A1 | 7/2018 | Allen | |
| 2018/0241736 A1 | 8/2018 | Sircana | |
| 2018/0268126 A1 | 9/2018 | Kaushik | |
| 2018/0270237 A1* | 9/2018 | Lewis | H04L 9/0894 |
| 2018/0270657 A1* | 9/2018 | Amisano | H04L 63/0861 |
| 2019/0050422 A1 | 2/2019 | Ono | |
| 2019/0068604 A1* | 2/2019 | Legault | H04L 63/0861 |
| 2019/0147667 A1 | 5/2019 | Susco et al. | |
| 2019/0286832 A1* | 9/2019 | Szeto | H04W 12/082 |
| 2019/0288995 A1 | 9/2019 | Bose et al. | |
| 2019/0313252 A1* | 10/2019 | Ting | H04W 76/10 |
| 2020/0151357 A1 | 5/2020 | Taniguchi | |
| 2020/0151976 A1* | 5/2020 | Keohane | G10L 15/22 |
| 2020/0242232 A1* | 7/2020 | Machani | H04L 63/0884 |
| 2020/0366685 A1 | 11/2020 | Ullrich | |
| 2020/0412741 A1 | 12/2020 | Shankar | |
| 2021/0075618 A1 | 3/2021 | Stephenson et al. | |
| 2022/0147634 A1 | 5/2022 | Silverstone | |

\* cited by examiner

DELAYED AND PROVISIONAL USER AUTHENTICATION FOR MEDICAL DEVICES

RELATED APPLICATIONS

This application is a continuation of U.S. Ser. No. 17/714,413, filed Apr. 6, 2022, which is a continuation of U.S. Ser. No. 16/414,943, filed May 17, 2019, the entire disclosure of each of which is hereby incorporated herein by reference.

FIELD OF THE INVENTION

In various embodiments, the present invention relates generally to user authentication to medical devices and, more specifically, to authentications that can be performed in a delayed or provisional manner.

BACKGROUND

Medical devices may require sophisticated setup and/or periodic adjustments in order to provide effective therapy and diagnostics to individual patients. Generally, the setup/adjustments involve the decisions of healthcare providers (e.g., doctors and nurses) and the real-time needs of the patients. Improper setup and/or faulty adjustments of medical devices may reduce the therapeutic effect, cause misdiagnosis and/or endanger the patients' lives. Thus, access to settings of the medical devices is often limited (e.g., using security authentications) in order to primarily protect the patient's well-being as well as privacy.

Common authentication methods in healthcare include the use of physical objects (such as radio-frequency identification (RFID) cards and/or keys), shared secrets (such as personal identification numbers (PINs) and/or passwords), and biometric technologies (such as voice prints, photos, signatures and/or fingerprints). While each of them may effectively condition use of the medical devices on proper authentication, they may be a hindrance to patient care in some situations. For example, a patient may need prompt treatment or immediate adjustment of settings of the medical device in critical life-threatening conditions. But if the on-scene healthcare providers must authenticate their identities before they can operate the devices, critical time may be lost—particularly if the authentication process goes awry. For example, the health provider may not have her RFID card with her, or she may forget the PINs or passwords for accessing specific medical devices. Even biometric technology may simply fail in some cases. For example, a wound on the caregiver's reference finger may cause false rejections and lock the provider out of the device.

Accordingly, there is a need for an authentication approach that allows the healthcare personnel to easily and promptly access medical devices, particularly in emergency situations, while still allowing the patient's well-being and privacy to be protected.

SUMMARY

Various embodiments hereof provide approaches for enabling a user (e.g., a clinician or a nurse) to access and manipulate a medical device before, during or after she authenticates her identity with the device. For example, the device may grant the user temporary access (e.g., 10 minutes or 30 minutes) to adjust its settings prior to receiving the authentication. In one implementation, the device may then require the user to provide authentication within a prescribed time interval subsequent to the operation of the device. Should the user fail to do so within the prescribed time, the device may reverse any changes made by the user and/or issue an alert to supervisory personnel. Accordingly, the present invention provides temporal flexibility to the user for providing authentication to permit prompt treatment to patients in urgent need of medical attention. In addition, the prescribed time interval may effectively protect the patient's safety and privacy.

In some embodiments, the medical device may require the user to at least provisionally authenticate prior to manipulating the device or its settings. In this situation, the user may provisionally authenticate using, for example, proximity technology. Upon receiving the provisional authentication, the device may grant the user temporary access, thereby allowing the user to immediately operate or adjust its settings. Again, the device may then prompt the user to provide her authentication within the predetermined time period. Should the user fail to complete/provide authentication within the prescribed time interval, the device may issue a reminder or an alert to the user or supervisory personnel and/or reverse any changes made by the user.

In addition, the device may create an audit trail storing a record of the user's interaction with the device. The audit trail may include an identification of the medical device, the time stamp (i.e., date and time) associated with each of the user's actions, the response of the device and actions undertaken therewith, etc. If the user is provisionally authenticated, her best known "identity" (e.g., the group she belongs to) may be made a part of the entry to the audit trail. By analyzing the audit trail, non-compliant events (e.g., a user's incorrect operation of the device and/or failure to provide authentication within the prescribed time interval) may be tracked. The audit trail may then allow appropriate personnel (e.g., the supervisor) to follow up with the user or user group that performed the non-compliant operations and/or are found to routinely do so. Accordingly, this approach may help the organization more efficiently educate its healthcare providers to be fully compliant with the authentication policy and/or the device's operation guide.

Accordingly, in one aspect, the invention pertains to a method of operating a secured device requiring user authentication. In various embodiments, the method includes receiving a request from a user for operating the device without prior authentication; granting the user temporary access to the device in accordance with a security policy, the security policy specifying a predetermined time interval and/or a predetermined number of device operations within which authentication must occur to continue at least some operations of the device; computationally storing an audit trail identifying the temporary access and actions performed during the temporary access; and upon determining that authentication has not been provided within the predetermined time interval or number of device operations, preventing at least some operations of the device and updating the audit trail to specify expiration of the temporary access. In one implementation, the temporary access allows the user to perform only some operations of the device.

The method may further include updating the audit trail to include a time of authentication upon authentication of the user within the predetermined time interval or number of device operations. In addition, the method may further include, upon determining that the user has failed to provide authentication within the predetermined time interval or number of device operations, causing (i) generation of an alert to the user or supervisory personnel and/or (ii) reversal of any adjustments to the device made by the user. In one embodiment, the method further includes accepting, as authentication, a permission remotely provided by previously authenticated personnel in accordance with an institutional security policy.

In various embodiments, the method further includes receiving provisional authentication, including user identification, from the user prior to granting the temporary access. The provisional authentication may be based on the user's proximity to the device without user action. In some embodiments, the audit trail includes an identification of the user, an identification of the device and a time stamp associated with each of the user's operations of the device. In addition, the predetermined time interval and/or predetermined number of device operations may be set dynamically. In one embodiment, the method further includes, upon determining that the user has failed to provide authentication within the predetermined time interval or number of device operations and receiving a request from a second user for operating the device, causing (i) generation of a message to the second user or supervisory personnel and/or (ii) reversal of any adjustments to the device made by the user.

In another aspect, the invention relates to a system for operating a secured device requiring user authentication. In various embodiment, the system includes a user interface for receiving a request from a user for operating the device; memory storing a security policy specifying a predetermined time interval and/or a predetermined number of device operations within which authentication must occur to continue at least some operations of the device; and a controller configured to grant, without prior authentication, the user temporary access to the device in accordance with the security policy; computationally store, in the memory, an audit trail identifying the temporary access and actions performed during the temporary access; and upon determining that authentication has not been provided within the predetermined time interval or number of device operations, prevent at least some operations of the device and update the audit trail to specify expiration of the temporary access. In one implementation, the temporary access allows the user to perform only some operations of the device.

The controller may be further configured to update the audit trail to include a time of authentication upon authentication of the user within the predetermined time interval or number of device operations. In addition, the controller may be further configured to upon determining that the user has failed to provide authentication within the predetermined time interval or number of device operations, cause (i) generation of an alert to the user or supervisory personnel and/or (ii) reversal of any adjustments to the device made by the user. In some embodiments, the memory further stores an institutional security policy; the controller is then further configured to accept, as authentication, a permission remotely provided by previously authenticated personnel in accordance with the institutional security policy.

In various embodiment, the system further includes a hands-free authentication system and/or a real-time location system (RTLS) for receiving provisional authentication, including user identification, from the user prior to granting the temporary access. The provisional authentication may be based on the user's proximity to the device without user action. In addition, the audit trail may include an identification of the user, an identification of the device and a time stamp associated with each of the user's operations of the device. In one embodiment, the controller is further configured to dynamically set the predetermined time interval and/or predetermined number of device operations. In some embodiments, the controller is further configured to cause, upon determining that the user has failed to provide authentication within the predetermined time interval or number of device operations and receiving a request from a second user for operating the device, (i) generation of a message to the second user or supervisory personnel and/or (ii) reversal of any adjustments to the device made by the user.

As used therein, the term "temporary" refers to a fraction (e.g., 1/10 or 1/20) of time that is necessary to complete a treatment procedure for a patient. In addition, reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
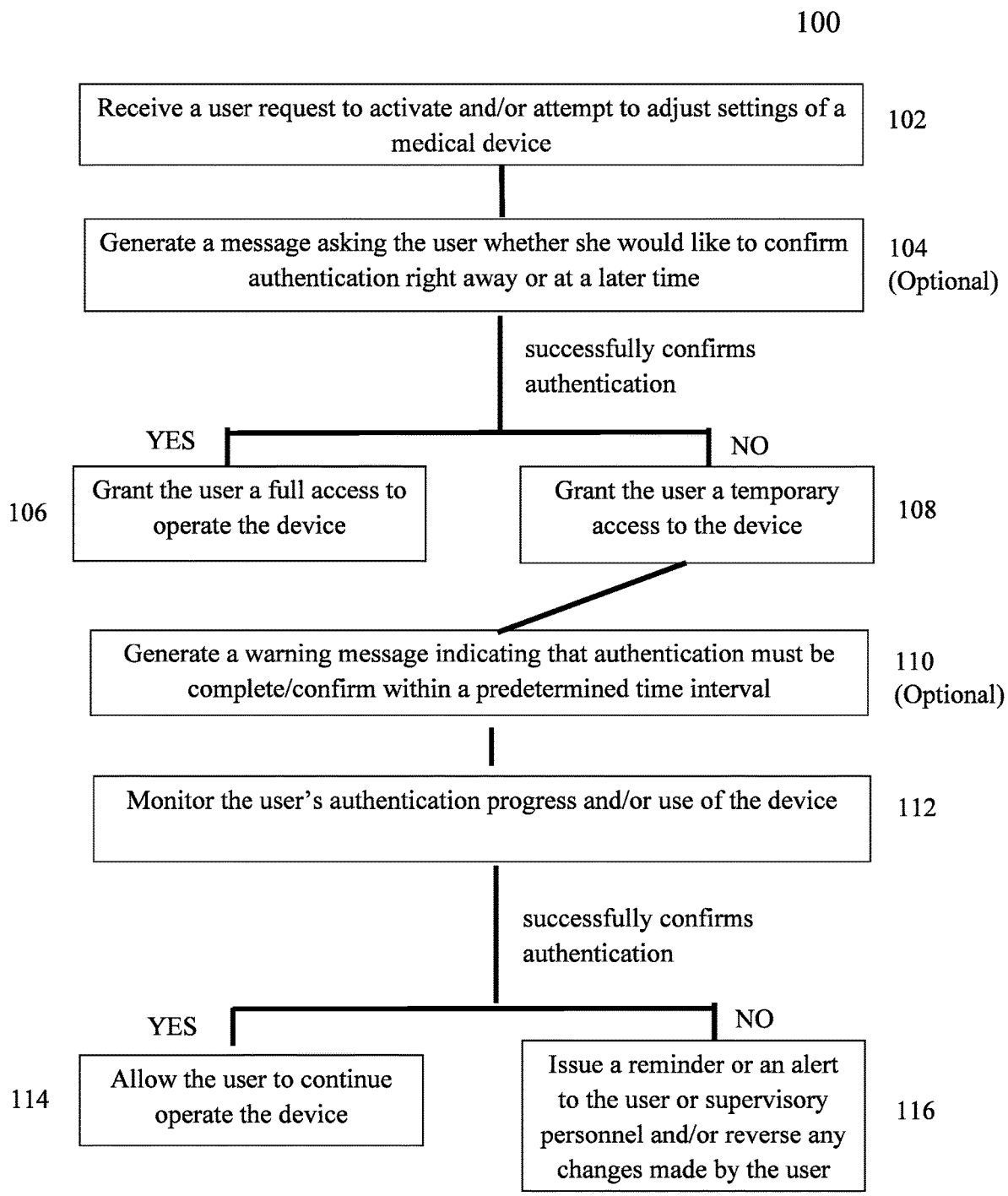
FIG. 1 is a flow chart of an exemplary authentication approach in accordance with various embodiments of the present invention.

FIG. 1 is a flow chart illustrating an exemplary authentication approach 100 in accordance with various embodiments. As shown, the authentication may begin, in step 102, with the user requesting activation and/or attempting to adjust the settings of a medical device by, for example, pressing a button or turning on a switch associated with the device. In step 104, upon receiving the user's request, a controller governing the functionality of the medical device may optionally generate a message asking the user whether she would like to provide authentication right away or at a later time. The user may respond via a user interface, such as a keyboard, a mouse or a touch-sensitive display. If the user selects an option to authenticate right away and successfully authenticates herself, the controller may grant the user full access to operate the device without any time constraints (in step 106). The user may authenticate using any suitable authentication approach that is supported by the medical device (and consistent with the security policy of the organization responsible for the medical device), such as provision of a username/password, passcode, RFID card, fingerprint biometrics, etc. Exemplary approaches for the user to authenticate her identity are provided, for example, in U.S. Pat. Nos. 8,973,091 and 9,246,902, the entire disclosures of which are hereby incorporated by reference.

If the user selects an option to authenticate later, the controller may immediately grant the user temporary access to the device so that the user can activate and operate of the device to treat a patient right away (in step 108). In one embodiment, the medical device provides a means (e.g., an emergency button/switch or a user interface item on a touch-sensitive display) for allowing the user to indicate that the need for operating the device is urgent; temporary access is granted only when urgency has been indicated by the user. Optionally, before or upon granting the temporary access, the controller may generate a warning message to the user indicating that the authentication process must be completed within a predetermined time interval or continued access will be terminated (in step 110). Subsequently, the controller may monitor the user's authentication progress and/or use of the device (in step 112). If the user successfully authenticates herself within the prescribed time interval, the controller may allow the user to continue operate the device without interruption or warning signals (in step 114). If, however, the user does not complete authentication within the prescribed time interval, the controller may issue a reminder or an alert to the user or supervisory personnel and/or reverse any changes made by the user as further described below (in step 116). This may advantageously protect the patient from any authenticated or malicious personnel (e.g., a family member, a child, etc.).

The controller may grant different levels of access to the user based on whether and when the authentication is provided. For example, the controller may grant full access to the user after she provides her authentication to enable the authenticated user to operate the entire functionality of the device. In contrast, the controller may grant limited access (e.g., only basic functionality) to the user before her authentication is provided. In some embodiments, the level of access to be granted is based on whether the situation is an emergency. For example, an unauthenticated user may be granted access to manipulate more (e.g., advanced) functionality of the medical device when the patient's need is urgent compared to the basic functionality to which access is accorded in non-emergency situations. In one embodiment, the level of access to be granted depends on the role of the user. For example, only a respiratory therapist may be granted access to perform complex changes in the settings of a ventilator.

In addition, the prescribed time interval within which the user must provide authentication to avoid termination of access may be device-dependent. For example, the prescribed time interval for a medical device that requires relatively more time to set up and/or adjust may be set longer than that for a device requiring relatively less time to set up and/or adjust. In one implementation, the prescribed time interval is determined based on an average time that the trained personnel take to complete the setup or adjustment of the device settings. In addition, the prescribed time interval may depend on the experience levels of the authenticated users. For example, if the majority of the healthcare providers in the emergency room have more than ten years of experience in operating the medical device, the prescribed time interval may be set relatively short. In contrast, if the majority of the healthcare providers in the emergency room have less than two years of experience in operating the medical device, the prescribed time interval may be set relatively long. Further, the prescribed time interval may depend on when the current software for operating the device was installed. For example, if the software was recently updated and the user interface has changed significantly, the controller may increase the prescribed time interval to provide the user additional time to complete the authentication process before generating an alert or terminating the access. Changes in the time interval may occur dynamically, e.g., in response to an event such as installation of new software, a change in device location or a change in personnel likely to operate the device.

Thus, compared to conventional approaches that require the user to provide authentication before operating the medical device, the present invention enables the user to complete the authentication process within a time duration between t and t+$\Delta$t, where the instance t represents the time when the user operates the device (e.g., changes the settings thereof) and $\Delta$t represents the prescribed grace period within which the user may operate the device prior to providing the authentication. This provides the temporal flexibility that permits urgent treatment to be delivered prior to authentication.

In some embodiments, instead of giving a prescribed time interval to the user to provide her authentication, the controller of the medical device may allow the user to perform certain operations or may allow certain events to occur prior to authentication. For example, ten steps may be required to set up the device for performing a treatment procedure; the controller may allow these steps to occur, regardless of the amount of time involved, before authentication is necessary to perform further restricted steps. This approach advantageously allows newly trained personnel to have sufficient time to complete the setup/adjustment of the medical device prior to authenticating themselves.

In some embodiments, the medical device may only act on the user's input upon the user pressing a specific button such as "Enter," "Run," "Submit," "Start," etc. In this case, the predetermined grace period may start when the user presses the specific button. This approach advantageously removes time pressure as she can take her time to enter device settings without fear of a timer running down.

In some embodiments, when the user fails to authenticate within the predetermined time interval or within the granted number of operations, the controller may initiate escalation responses. For example, the controller may first issue an auditable reminder or alert to the user. Additionally or alternatively, the controller may escalate the alert to a dedicated care team and/or a supervisor through various means, e.g., via the CORTEXT system (a secure communication platform marketed by Imprivata Inc., https://www.imprivata.com/secure-communications), Page, short message service (SMS), and/or a clinical application. Upon receiving the alert, the supervisor or any member of the care team may approach the device, authenticate herself into the device, and authorize, override or reverse the operations performed by the unauthenticated user in accordance with an institutional security policy. The institutional security policy may specify, for example, a clinical role of the supervisor and a list of users whose operations the supervisor may authorize, override or revise. In one embodiment, the authorization/override can be remotely performed. For example, the medical device may be electronically connected to an electronic medical record (EMR) application, and the controller may flag the unauthenticated operations of the device within the EMR environment. Upon receiving the flag, an authorized user (e.g., the supervisor and/or dedicated caregiver) authenticated by the EMR application may remotely authorize the operations based on the EMR authentication or override/reverse the changes made by the unauthenticated user. In one implementation, the controller sends the alert to members of the care team using CORTEXT. Because the alert may, in some embodiments, include the operations performed by the unauthenticated user as well as the user's identity, the supervisor/dedicated caregiver may more easily make the decision whether to authorize or to override/reverse the operations. Alternatively, if the user initiating the operations is already authenticated by an approved (e.g., EMR) application, this authentication may be transferred (e.g., via CORTEXT) to the medical device. The authentication modalities supported by the application may be the same or different from those supported by the medical device.

In some embodiments, the medical device is expensive and/or provides treatment critical to the patient; incorrect operation of the device may cause severe damage to the device and/or may be life-threatening to the patient. Accordingly, it may be preferred to require a provisional or less demanding authentication before the user is allowed to operate the device and/or make any changes in its settings under emergency conditions. The provisional authentication may, for example, confirm only that the user is a member of the healthcare team in the organization and not reveal the specific identity of the user. This approach may prevent the device from being operated by untrained personnel (e.g., the patient's family members) or maliciously. In addition, the controller may, again, give the provisionally authenticated user a prescribed grace period to fully authenticate before initiating any of the escalation responses described above.

Figure 2:
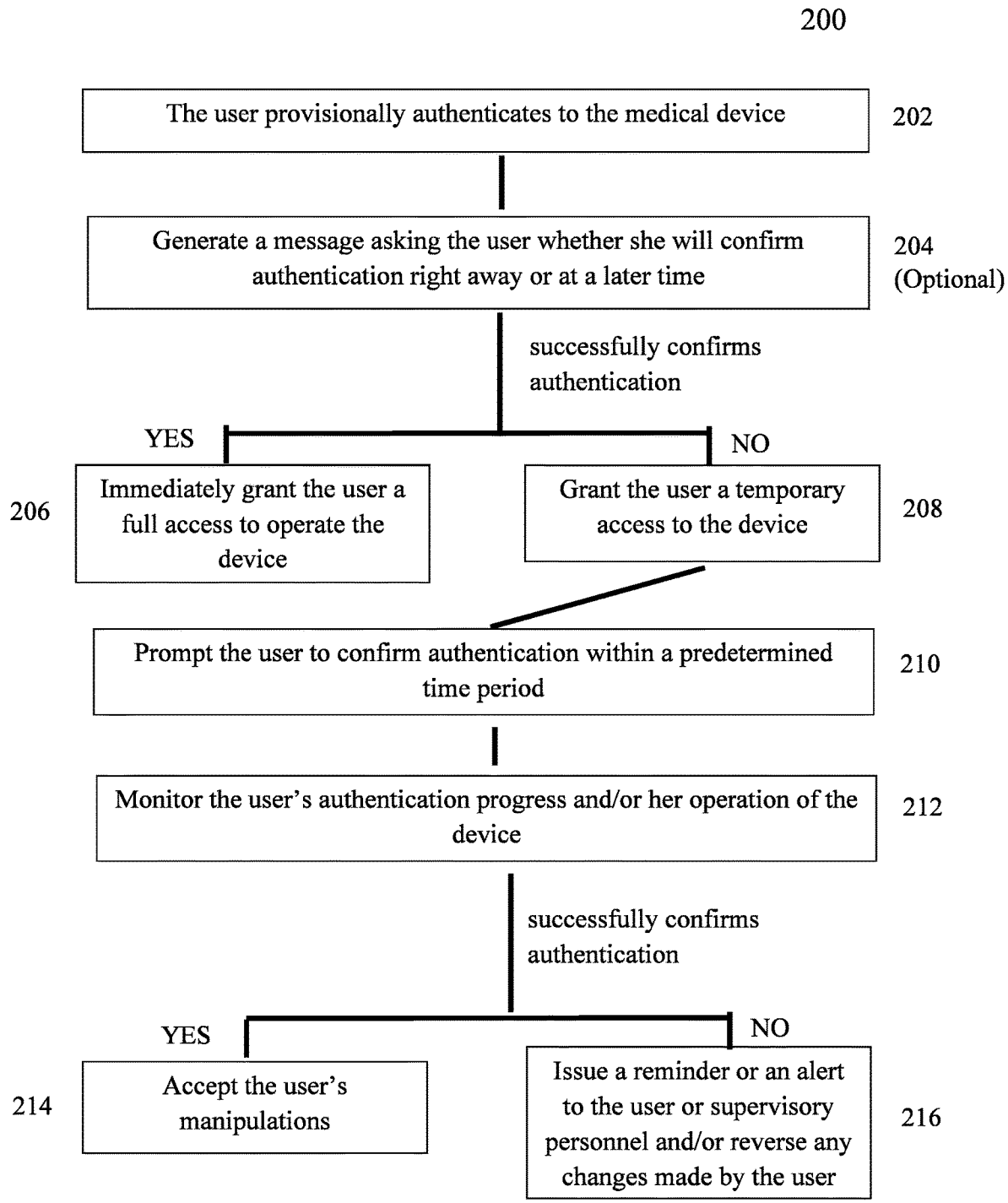
FIG. 2 is a flow chart of an exemplary authentication approach in accordance with various embodiments of the present invention.

FIG. 2 is a flow chart illustrating an exemplary authentication approach 200 for a medical device that requires at least provisional authentication prior to operation. In step 202, prior to setting up and/or adjusting settings of the medical device, the user may provisionally authenticate herself using any suitable approach (e.g., proximity technology). For example, the medical device may implement a hands-free authentication system or utilize a real-time location system (RTLS) that enables the user to provisionally authenticate via a mobile device, a tag, a badge, etc. Typically, the user is not required to actively initiate the provisional authentication. For example, in the hands-free-authentication system, the user may be provisionally authenticated using a suitable security application (e.g., employing one-time passwords) active on the user's mobile device when the mobile device is locked and/or in the user's pocket. Because the provisional authentication may not uniquely identify the user and, moreover, may allow a malicious person to operate the device by taking advantage of his proximity to the user, the device may require a more reliable form of authentication within a predetermined time interval as described above. Thus, the device may optionally generate a message asking whether the user will provide authentication right away or at a later time (in step 204). If the user selects an option to authenticate immediately and successfully authenticates her identity, the device may immediately grant the user full access to the device (in step 206). If, however, the user selects an option to provide authentication later, the device may grant the user temporary access, thereby allowing the user to immediately operate the device and/or adjust its settings (in step 208). But the device may prompt the user to provide her authentication within a predetermined time period (in step 210) and subsequently monitor the user's authentication progress and/or her operation of the device (in step 212). For example, the user may provide her authentication by sending a push token or using any authentication modality described above. Alternatively, the controller of the device may flag the missing authentication in an application (e.g., EMR) that the user currently or routinely uses and is authenticated; the user may then complete the authentication using the application. After the user successfully provides authentication within the prescribed time interval, the controller may accept her manipulations and issue no interruption or warning signals (in step 214). If, however, the user fails to complete authentication within the prescribed time interval, the controller may employ one or more escalation responses (e.g., issue a reminder or an alert to the user or supervisory personnel and/or reverse any changes made by the user) (in step 216).

In some embodiments, the medical device implements a CORTEXT authentication system. Thus, when the user is provisionally authenticated at the device, the device may send a CORTEXT challenge to the user. In addition, when the provisionally authenticated user (or an anonymous person) operates the medical device, the medical device may send a CORTEXT challenge to other personnel (e.g., the supervisor and/or other members of a healthcare team) to validate the user's operation of the device, thereby sparing the user the need to fully authenticate; in effect, the other personnel (who have authenticated themselves in a manner satisfying the security policy for the medical device) "vouch" for the provisionally authenticated user. Again, the context of the challenge may include the performed operations involving the device and/or the user's identity (to the extent known from the provisional authentication). CORTEXT may then display buttons (e.g., "accept," "undo," "ignore," etc.) to enable the other personnel to select different actions affecting the user's operation of the device. Based on the selection, the controller of the device may accept, reverse or ignore the user's entire or partial manipulations.

Figure 3:
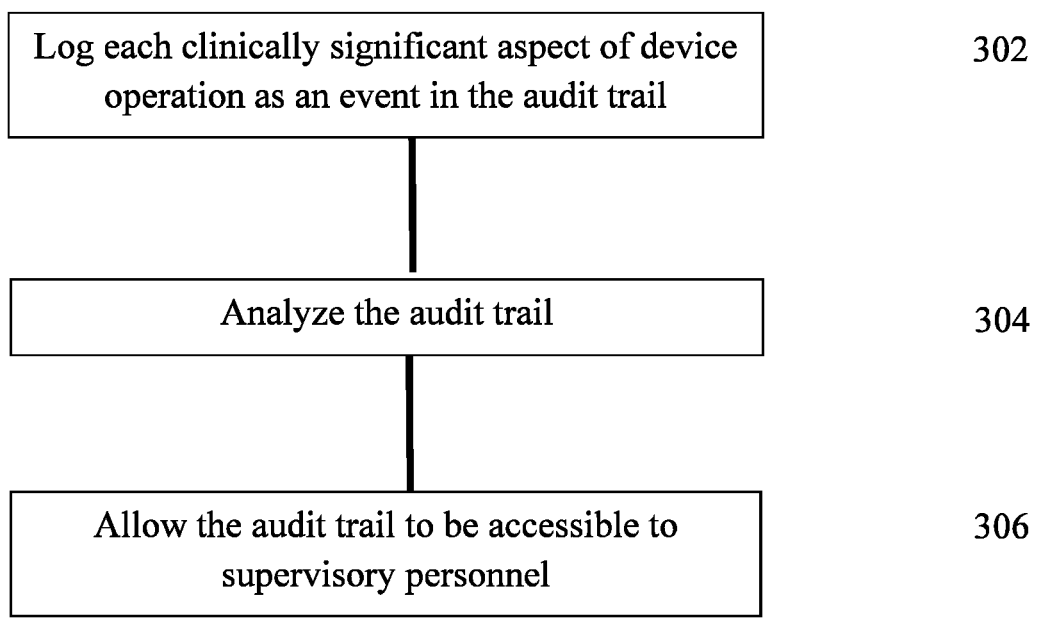
FIG. 3 is a flow chart of an exemplary authentication approach in accordance with various embodiments of the present invention.

In various embodiments, the provisional authentication is sufficient to allow the user to operate the device and there is no need for further authentication. Alternatively, authentication may not even be required to operate the device. Relaxed authentication control may be suitable for devices that are inexpensive and/or that provide non-critical treatment to the patient. Referring to FIG. 3, regardless whether and what authentication is required to operate the medical device, in various embodiments, the device may create an audit trail. For example, each clinically significant aspect of device operation may be logged as an event in the audit trail (in step 302), which is stored in memory. As used herein, the term "audit trail" refers to a record of device operation, including the identity of the device and the user, operations performed, events detected, and the times thereof, and may include further state information such as the location of the device, the identities of other detected personnel, etc. If the user has been only provisionally authenticated, her best known "identity" (e.g., the group she belongs to) may suffice for the audit trail. By analyzing the audit trail, non-compliant events (e.g., user's incorrect operation and/or failure to provide authentication within the prescribed time interval) may be tracked (in step 304). Each user's records may be monitored for excessive numbers of non-compliant events, with appropriate actions taken manually or automatically by the system. For example, one provisional authentication may not trigger any oversight action, but multiple provisional authentications within a short period, or provisional authentications not followed by proper authentications, may result in the reduction of a user's privilege level within the institution pending sign-off by supervisory personnel. Making the audit trail accessible to supervisory personnel (in step 306) allows them to identify and counsel persistently non-complaint subordinates. This approach may help the organization more efficiently educate its healthcare providers in institutional policy. Accordingly, various embodiments advantageously strike a balance between safety of the patient, auditability and necessary device access.

In some embodiments, consecutive operation of the medical device by different users may create inaccurate audit trails. For example, the first user may have submitted provisional changes in the settings of the medical device without completing/providing authentication within the prescribed time interval. When a subsequent user attempts to adjust the settings of the medical device and successfully completes/provides authentication, the audit trails may associate the subsequent user with all cumulative changes, including the changes she made as well as the provisional changes made by the previous user. In addition, the subsequent user may accidentally approve the changes made by the previous user when accessing the medical device, which, again, improperly associates the subsequent user with the change made by the previous user in the audit trail. This problem may be further aggravated when the subsequent user cannot easily or clearly see the changes made by the previous user.

To delineate where the responsibility of the first user terminates and that of the second user starts, in various embodiments, the medical device may display a message to the user indicating that the current settings are unauthenticated inputs. The subsequent user may press a button (e.g., as described in step 102) and/or take suitable action to terminate the previous user session. Any changes that had been submitted previously may then be flagged as "final but not authenticated" without being associated with the subsequent user in the audit trail. Additionally, the controller may reverse any changes made by the unauthenticated user and/or issue a reminder or an alert to the subsequent user or supervisory personnel as described above. Again, the supervisory personnel may remotely authorize or override the changes. Accordingly, various embodiments advantageously provide accountability as to which caregiver did what and when. This can help with legal and/or compliance issues (including protecting nurses from being implicated if in fact another nurse or physician made changes) and with detecting the need for training of individual caregivers.

Figure 4A:
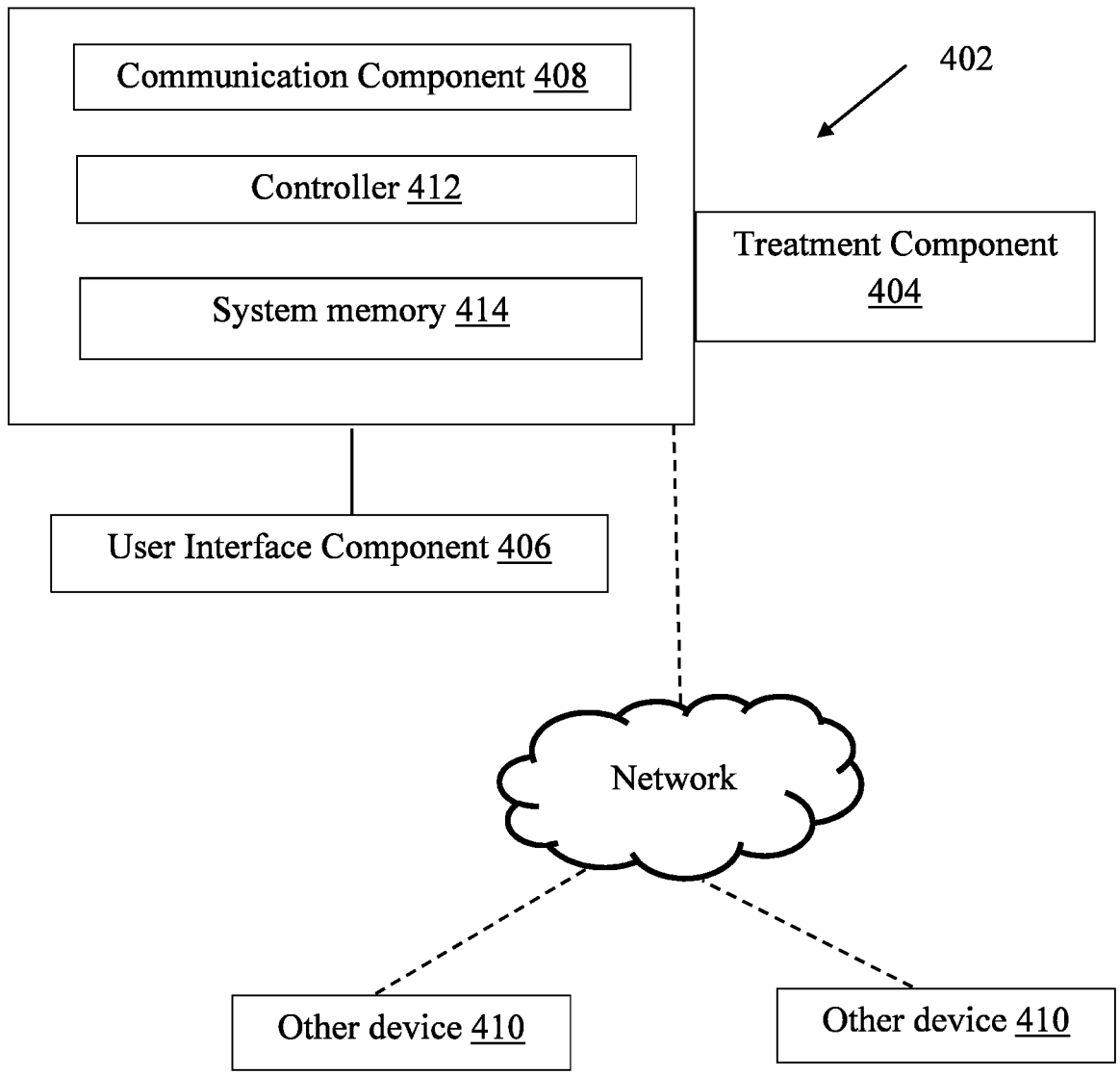
FIGS. 4A and 4B schematically illustrate an exemplary medical device in accordance with various embodiments of the present invention.

FIG. 4A illustrates an exemplary medical device 402 in accordance with embodiments of the present invention. The device 402 may be a smart infusion pump, a ventilator or any other type of medical device capable of providing treatment to a patient. As depicted, the device 402 may include a treatment component 404 for providing treatment to the patient, a user interface component 406 (e.g., a screen, a front panel, a keyboard and/or a mouse) for allowing the user to operate the device 402, a communication component 408 (e.g., a modem, a network interface or other communication mechanism) designed to provide communications with a network—such as the Internet and/or any other land-based or wireless telecommunications network or system—and, through the network, with other devices 410 (such as a remote server, a user's device, or another medical device). The remote server and/or the user's device (e.g., a mobile device) may be configured to authenticate the user for permitted operation of the medical device 402; exemplary configurations of the remote server and/or user's device are provided, for example, in U.S. Pat. Nos. 8,973, 091 and 9,246,902, the entire disclosures of which are hereby incorporated by reference.

In addition, the medical device 402 may include a controller 412 for controlling the functionality of the device 402 and system memory 414 including instructions, conceptually illustrated as a group of modules, that control the operation of controller 412 and its interaction with the other hardware components. The controller 412 executes commands and instructions and may be a general purpose computer, but may utilize any of a wide variety of other technologies including a special purpose computer, a microcomputer, minicomputer, mainframe computer, programmed microprocessor, micro-controller, peripheral integrated circuit element, a CSIC (customer-specific integrated circuit), ASIC (application-specific integrated circuit), a logic circuit, a digital signal processor, a programmable logic device, such as an FPGA (field-programmable gate array), PLD (programmable logic device), PLA (programmable logic array), RFID processor, smart chip, or any other device or arrangement of devices that is capable of implementing the approaches described in FIGS. 1-3.

Figure 4B:
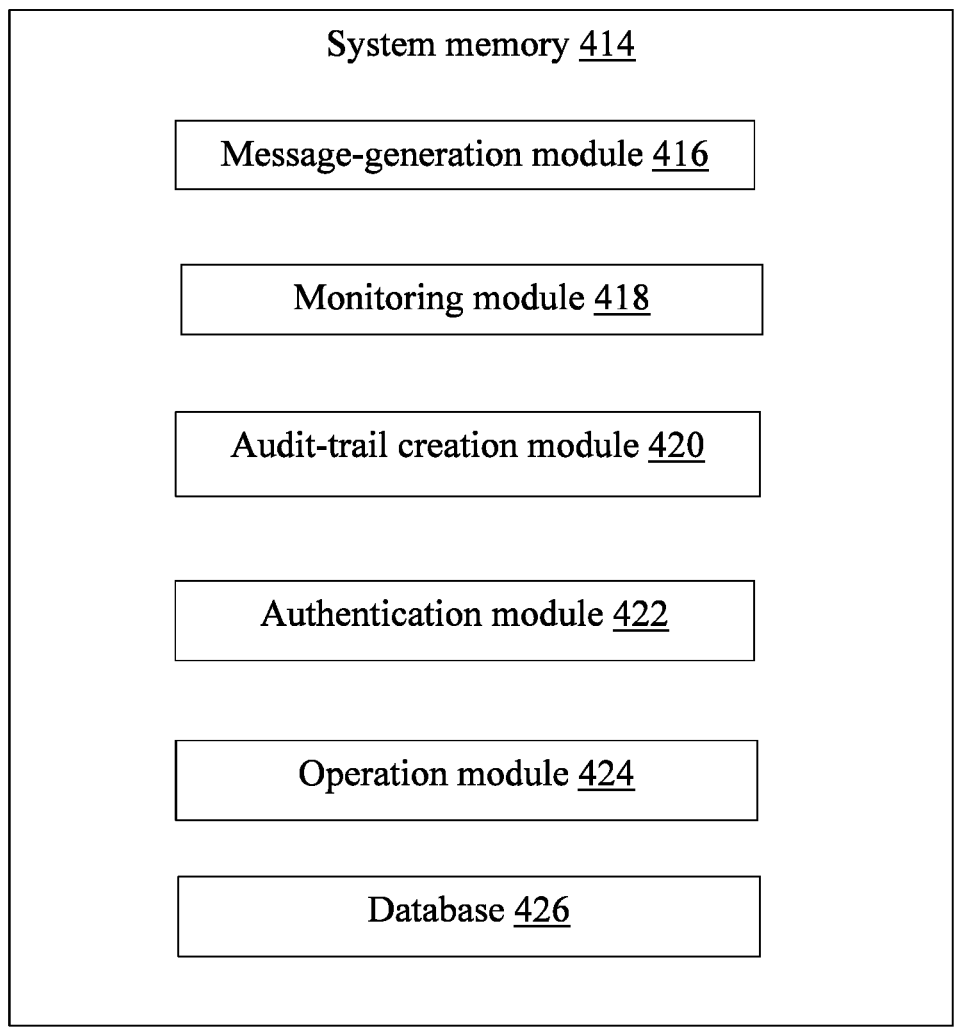

With reference to FIG. 4B, the system memory 414 may include a message-generation module 416 for generating messages to the user, a monitoring module 418 for monitoring the user's authentication progress and/or her operation of the device, an audit-trail creation module 420 for creating an audit trail associated with manipulations of the device, an authentication module 422 for determining whether the user has provided authentication by, for example, comparing the received user information against information stored in an authentication information database and/or an authentication policy and, based thereon, granting the user access to the device, an operation module 424 for accept, reject or ignore the user's manipulations of the treatment component 404 and/or transmit an alter to the supervisory personnel. In addition, the system memory 414 may include a database 426 storing the security policy and/or institutional security policy as described above. Alternatively, the databased 426 may be included in a storage device (not shown) accessible to the controller 412 via, for example, the communication component 408. The various modules may be programmed in any suitable programming language, including, without limitation, high-level languages such as C, C++, C#, Ada, Basic, Cobra, Fortran, Java, Lisp, Perl, Python, Ruby, or Object Pascal, or low-level assembly languages; in some embodiments, different modules are programmed in different languages. As will be readily understood by a person of skill in the art, the computational functionality required to carry out authentication methods in accordance herewith may be organized (in software modules or otherwise) in many different ways, and the depicted embodiment in FIGS. 4A and 4B is, therefore, not to be regarded as limiting.

In addition, the controller 412 and memory 414 may be implemented in a server remote from the medical device 402 and perform the functionality relating to user authentication and operations of the device 402 as described above via the communication component 408. Further, the authentication approaches described above may not be limited to medical devices; any suitable devices may implement the authentication approaches described herein are thus within the scope of the present invention.

In general, the terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of operating a secured device, the method comprising:

receiving a request from a user for operating a device that requires an authentication to operate the device, without receiving the authentication to operate the device before or in connection with the request, the request being associated with at least one of (i) a level of urgency or (ii) a role of the user;

granting the user temporary access to the device responsive to the request from the user and without receiving the authentication, including granting a level of the temporary access based on the at least one of the level of urgency or the role of the user;

computationally storing an audit trail identifying the temporary access and actions performed during the temporary access; and upon determining that authentication has not been provided by the user prior to expiration of the temporary access, preventing at least some operations of the device and updating the audit trail to specify expiration of the temporary access.

2. The method of claim 1, wherein the level of the temporary access corresponds to access to full functionality of the device when the request specifies an emergency level of urgency.

3. The method of claim 1, wherein the level of the temporary access corresponds to access to only partial functionality of the device when (i) the request specifies a non-emergency level of urgency or (ii) a level of urgency is not specified in the request.

4. The method of claim 1, wherein the temporary access is granted without requiring validation from another user.

5. The method of claim 1, wherein the temporary access is granted without uniquely identifying the user.

6. The method of claim 1, wherein the request does not uniquely identify the user.

7. The method of claim 1, wherein the temporary access is granted in accordance with a security policy, the security policy specifying at least one of (i) a predetermined time interval within which authentication must occur to continue at least some operations of the device or (ii) a predetermined number of device operations within which authentication must occur to continue at least some operations of the device.

8. The method of claim 7, wherein the predetermined time interval and/or predetermined number of device operations is set dynamically.

9. The method of claim 7, wherein the predetermined time interval and/or predetermined number of device operations depends upon at least one of (i) a type of the device or (ii) a complexity of the device.

10. The method of claim 7, further comprising updating the audit trail to include a time of authentication upon authentication of the user within the predetermined time interval or number of device operations.

11. The method of claim 1, further comprising updating the audit trail to include a time of authentication upon authentication of the user prior to expiration of the temporary access.

12. The method of claim 1, wherein the level of the temporary access never corresponds to access to full functionality of the device, access to full functionality of the device being provided to the user only after authentication is provided.

13. The method of claim 1, further comprising, upon determining that the user has failed to provide authentication prior to expiration of the temporary access, causing at least one of (i) generation of an alert to the user or supervisory personnel or (ii) reversal of any adjustments to the device made by the user.

14. The method of claim 13, further comprising accepting, as authentication, a permission remotely provided by previously authenticated personnel in accordance with an institutional security policy.

15. The method of claim 1, further comprising receiving provisional authentication from the user prior to granting the temporary access.

16. The method of claim 15, wherein the provisional authentication includes an identification of the user.

17. The method of claim 15, wherein the provisional authentication is based on the user's proximity to the device without user action.

18. The method of claim 1, wherein the audit trail includes an identification of the device and a time stamp associated with each of the user's operations of the device.

19. The method of claim 18, wherein the audit trail includes an identification of the user.

20. The method of claim 1, further comprising, upon determining that the user has failed to provide authentication prior to expiration of the temporary access and upon receiving a request from a second user for operating the device, causing at least one of (i) generation of a message to the second user or supervisory personnel or (ii) reversal of any adjustments to the device made by the user.

* * * * *